United States Patent [19]
Seltzer et al.

[11] Patent Number: 4,740,205
[45] Date of Patent: Apr. 26, 1988

[54] DISPOSABLE NEEDLE SYSTEM

[76] Inventors: Leilani Seltzer, 1001 Grandview Dr., Nashville, Tenn. 37204; Thomas B. Shiu, 7623 Sussex Creek Dr., Apt. #204, Darien, Ill. 60559

[21] Appl. No.: 76,617

[22] Filed: Jul. 23, 1987

[51] Int. Cl.[4] .............................................. A61M 5/32
[52] U.S. Cl. ..................................... 604/192; 604/241
[58] Field of Search .............. 604/192, 263, 240, 241, 604/187; 206/365

[56] References Cited

U.S. PATENT DOCUMENTS

| | | | |
|---|---|---|---|
| 3,052,241 | 9/1962 | Myerson et al. | 604/192 |
| 3,344,787 | 10/1967 | MacLean | 604/241 |
| 4,237,882 | 12/1980 | Wickham | 604/192 |

Primary Examiner—John D. Yasko
Attorney, Agent, or Firm—Mason, Kolehmainen, Rathburn & Wyss

[57] ABSTRACT

A new and improved disposable needle system includes apparatus for receiving/dispensing fluids such as body fluids, medicaments, vaccines and the like comprising a disposable needle assembly having a removable cap for protecting an open outer end of an elongated metal needle and a removable inner end cap for enclosing an inner end portion of the needle. The needle is provided with a threaded plastic mount fixed intermediate the ends and the mount is threaded into an aperture in a forward wall of a tube holder adapted to receive and support a hollow tube in communication with the inner end portion of the needle when inserted into the interior of the tube holder with the mount threaded into the aperture in preparation for use. The tube holder includes a needle mount engaging sleeve or wrench permanently affixed and rotatably mounted on the forward end of the holder. The rotary sleeve comprises an open-ended socket-wrench-like device for rotating the needle mount to release the needle from the tube holder after use without requiring any human contact with the needle itself. In preparation for use, the inner end cap is removed and the uncovered mount is threaded into the aperture of the tube holder by rotating the outer cap, again without requiring manual contact with any portion of the needle or mount. When the needle is fully inserted into the tube holder, and thereafter when the needle is ready for use, the cap is removed to expose the outer end of the needle. The outer end cap has a one way clutch engaging the needle mount and the cap cannot be used for unthreading the needle after use. For this purpose, only the rotary sleeve may be used and this helps to insure that no inadvertent contact with a contaminated needle results as the needle is disposed of.

20 Claims, 3 Drawing Sheets

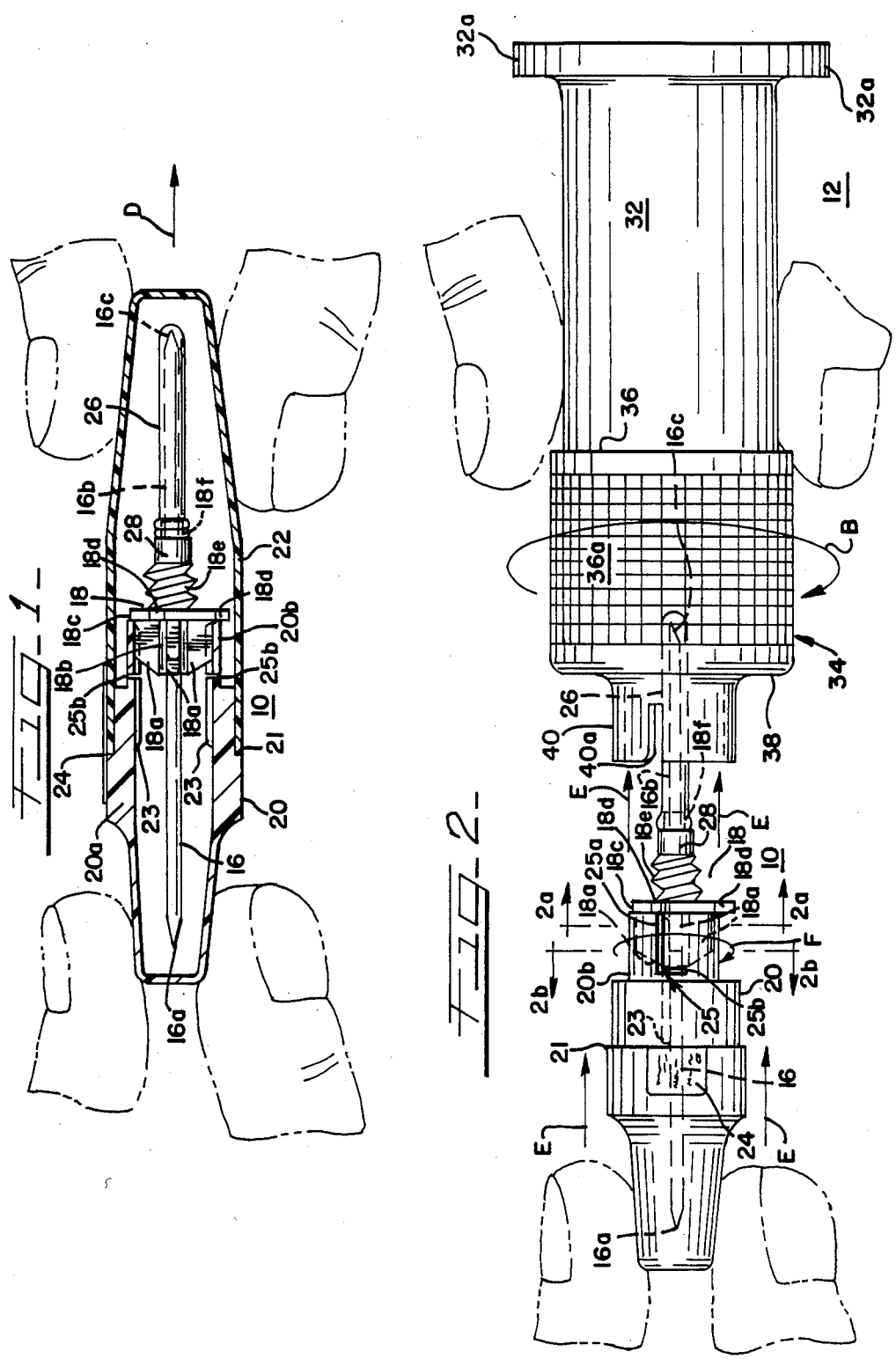

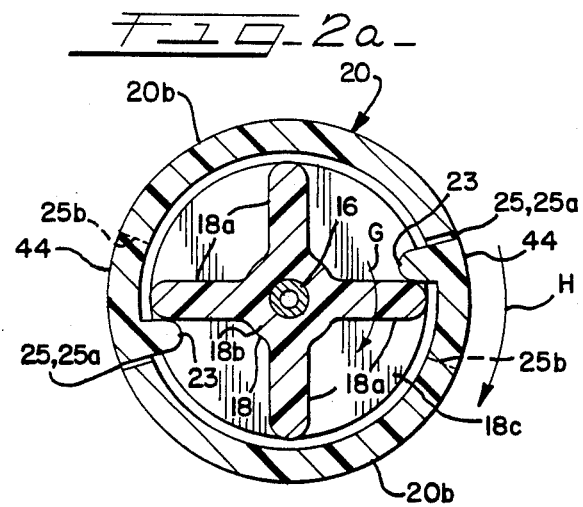
FIG-2a-
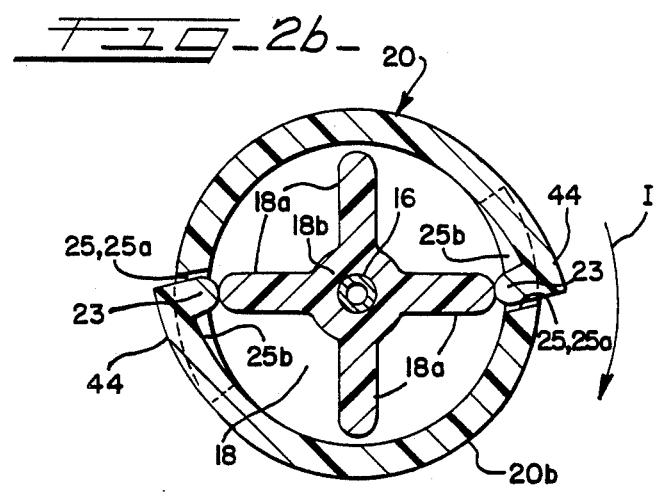
FIG-2b-

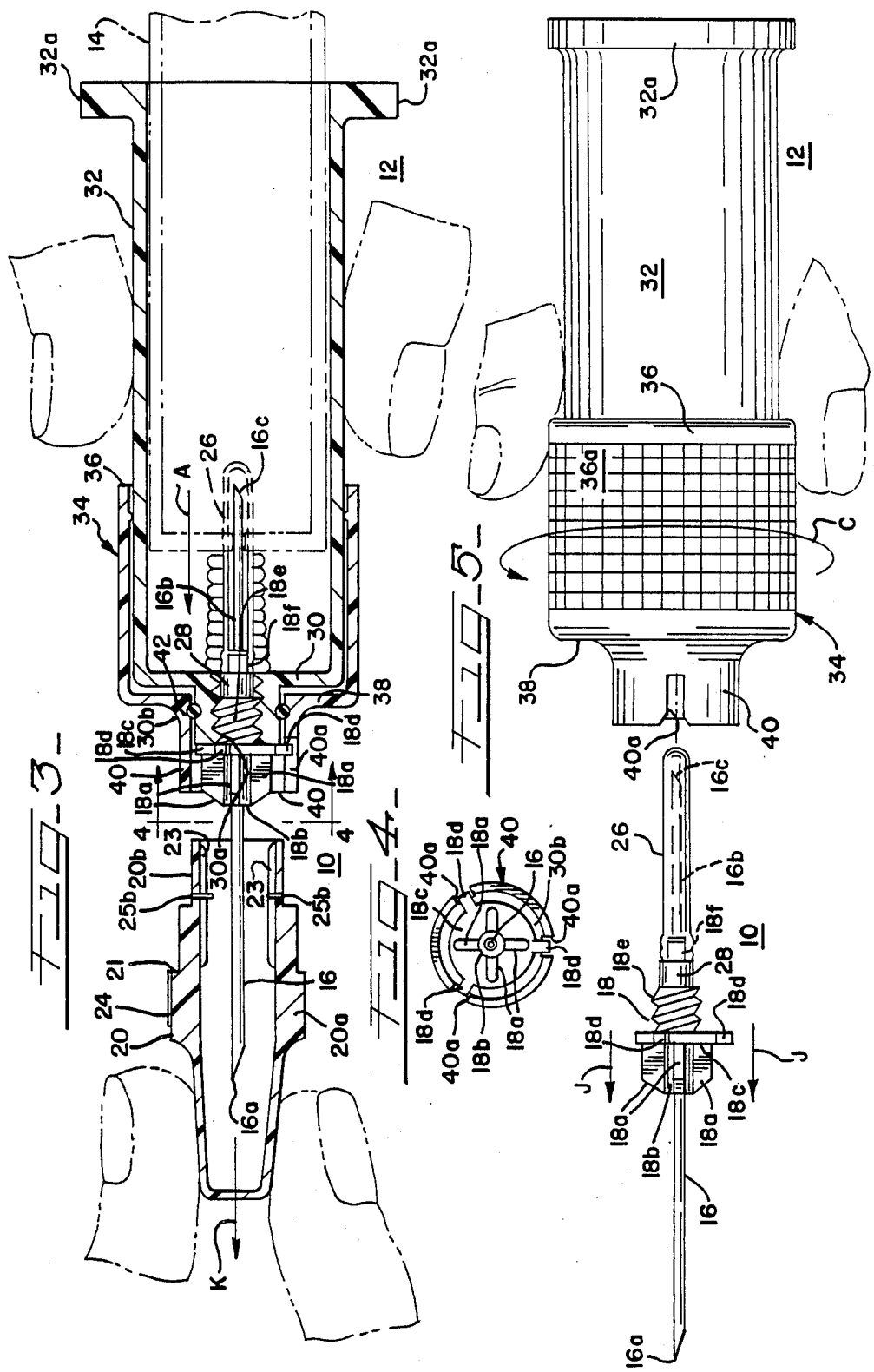

DISPOSABLE NEEDLE SYSTEM

BACKGROUND OF THE INVENTION

1. Field of the Invention

The present invention relates to a new and improved disposable needle system especially adapted for receiving/dispensing fluids such as body fluids, medicaments, vaccines and the like. The disposable needle system provides for initially setting up a needle assembly ready for receiving/dispensing fluids and thereafter when the fluids have been collected or injected, the used needle is disposed of without ever requiring human contact therewith. The system thus provides an extremely safe and sterile system for the injection of fluids into the body and for sampling or collecting of fluids.

2. Background of the Prior Art

Needle stick injuries occur commonly and pose a threat to the health of hospital personnel and personnel in doctors' offices and dispensaries. The majority of these injuries occur during needle disposal activity and until recently the most common needle disposal system utilized in United States hospitals entailed the snipping off of a used needle and the placement of a snipped off needle in a "cutter" collection box while depositing the syringe in a separate disposable cardboard container.

Studies have revealed that when some needle cutting or snipping devices are used, contaminating fluid thereon may be aerosolized or splattered into the environment and onto environmental surfaces. In addition, reusable collection boxes, cutters or snippers must often be emptied, cleaned and periodically inspected, and all of these manipulations increase the likelihood of contaminating exposure to personnel and the environment.

Many state laws require that needles and syringes be rendered inoperable for future use and in some cases there are requirements that the used needles and syringes must be placed in a puncture and leakproof container which must eventually be autoclaved or incinerated. With increasing concern for the possibility of inadvertent contraction of blood transmittable diseases such as hepatitis, syphillis and now AIDS, a safer means of blood and other body fluid collection is of the utmost importance to health care professionals and workers worldwide.

The following U.S. patents disclose various hypodermic syringes, needle assemblies, and coupling elements which have been developed over the years:

Haines U.S. Pat. No. 1,591,761
Eisele U.S. Pat. No. 2,020,111
Kouffman U.S. Pat. No. 2,047,512
Burnside U.S. Pat. No. 2,604,890
MacGregor U.S. Pat. No. 2,695,613
Lingley U.S. Pat. No. 2,806,473
Debaz U.S. Pat. No. 2,829,643
Cosentino et al U.S. Pat. No. 4,123,091
Schultz et al U.S. Pat. No. 4,326,516
Silvern U.S. Pat. No. 4,490,142

OBJECTS OF THE INVENTION

It is an object of the present invention to provide a new and improved disposable needle system and more particularly a new and improved disposable needle system which eliminates or greatly reduces the possibility of needle stick injury during preparation, use and/or disposal of a needle after use.

Yet another object of the present invention is to provide a new and improved disposable needle system of the character described which is safe and easy to use and which does not require human contact with a needle, either before or after use and disposal.

Another object of the present invention is to provide a new and improved disposable needle system wherein the need for recapping or covering of a needle after use is completely eliminated.

Another object of the present invention is to provide a new and improved disposable needle system of the character described which permits a used needle to be easily disposed of and disengaged from a tube holder in a simple, fast and sterile manner.

Another object of the present invention is to provide a new and improved disposable needle system which only requires one hand for use during the reception or dispensing of fluids and during the disposal of a used needle.

Another object of the present invention is to provide a new and improved disposable needle system which eliminates or greatly reduces the shortcomings and disadvantages of prior art systems.

Still another object of the present invention is to provide a new and improved disposble needle assembly which is economical to manufacture and which does not require a high degree of skill for safe and sterile usage.

BRIEF SUMMARY OF THE INVENTION

The foregoing and other objects and advantages of the present invention are accomplished in an illustrated embodiment comprising a disposable needle system for receiving/dispensing fluid such as body fluids, medicaments, vaccines and the like. The system includes an elongated, hollow, metal needle having a removable outer end cap for the outer end portion and removable inner end cap for an inner end portion of the needle. Intermediate the ends, the needle is provided with a threaded mount adapted to be threaded into an aperture in a forward end wall of a tube holder when the inner end portion of the needle is inserted into the holder in preparation for use after the inner end cap has been removed. The tube holder is adapted to receive and support a tube or container for fluid and the needle mount is threaded into the aperture in the formed wall of the holder by rotating the outer end cap until the inner end of the needle is fully seated and the tube is fully inserted into the holder ready for use. The outer end cap is not withdrawn from the needle until the time the needle is is to be used.

A needle mount engaging sleeve or wrench is rotatably mounted on the forward end of the tube holder and is directly engageable with the needle mount for unthreading the needle mount from the aperture in the forward end wall of the tube holder after the needle is used. This arrangement eliminates the need to replace the cap on the outer end of a used or contaminated needle for the purpose of disposing of the needle. A one-way clutch is provided on the outer needle cap so that the cap can only be used for threading the needle mount into the tube holder, but cannot be used for unthreading the needle mount after the needle is mounted on the tube holder. Only the rotatable sleeve can be used for this purpose after a needle has been attached to the tube holder. The rotatable sleeve is manually rotatable to disengage the needle mount from the tube holder without requiring manual contact or touching of any portion of the needle and/or mount. Once the needle mount is unthreaded with the sleeve, the disposable, contaminated needle is free to drop away from the tube holder into a suitable collection receptacle.

BRIEF DESCRIPTION OF THE DRAWINGS

For a better understanding of the present invention, reference should be had to the following detailed description taken in conjunction with the drawings, in which:

FIG. 1 is a side elevational view, with portions shown in longitudinal section, of a new and improved disposable needle in accordance with the features of the present invention;

FIG. 2 is a longitudinal elevational view of the needle after removal of the inner end cap and illustrating the needle being threaded into the end of a tube holder in preparation for use;

FIG. 2a is a transverse cross-sectional view taken along lines 2a—2a of FIG. 2;

FIG. 2b is a transverse cross-sectional view taken along lines 2b—2b of FIG. 2;

FIG. 3 is a longitudinal elevational view of the tube holder with the needle fully inserted and ready for use with the outer end cap being removed;

FIG. 4 is a transverse cross-sectional view taken substantially along lines 4—4 of FIG. 3; and FIG. 5 is a longitudinal elevational view illustrating a used needle after disengagement from the tube holder for disposal in a safe, efficient and sterile manner.

DETAILED DESCRIPTION OF THE PRESENT INVENTION

Referring now more particularly to the drawings, in FIG. 1 is illustrated and new and improved disposable needle assembly 10 constructed in accordance with the features of the present invention. The disposable needle assembly is adapted to be used with a reuseable tube holder 12 to complete a system especially designed to receive or dispense fluids such as body fluids, medicaments, vaccines and the like in a safe and sterile manner. More particularly, the disposable needle and the tube holder 12 are adapted for taking and receiving blood or other fluids from humans or animals and the fluids taken are collected within or dispensed from a conventional, hollow tubular container or tube 14 which is inserted into the hollow tube holder 12 as shown in FIG. 3 by the arrow "A".

The disposable needle system of the present application is an improvement on the DISPOSABLE NEEDLE SYSTEM shown and described in copending U.S. patent application Ser. No. 31,364, filed Mar. 30, 1987.

The disposable, needle assembly includes an elongated, thin, hollow metal needle 16 preferably formed of stainless steel and having a sharp tip or outer end 16a open to receive or dispense fluids and an inner end portion 16b having a sharp inner end or tip 16c which is likewise open to dispense or receive fluid to or from the tube 14 placed within the tube holder 12. Intermediate the opposite ends, the needle is provided with an annular mount 18 preferably formed of resinous plastic material and molded in place on the outer surface of the elongated metal needle.

The needle assembly 10 also includes a removable outer end cap 20 and a removable inner end cap 22, both of which caps are removed from the needle before use. Preferably, the outer and inner end caps are formed of molded resinous plastic material and both include an elongated hollow body having an integrally formed circular end wall at an outer end and an opposite, open, inner end. The tubular hollow body of each end cap has has an inside diameter at the open end that is slightly greater than the maximum outside diameter of the needle mount 18.

The outer end cap 20 and the inner end cap 22 are somewhat different in shape as shown in FIG. 1 and when assembled together provide a complete protective, sterile enclosure for the needle 16 and its mount 18. The outer end cap is formed with a relatively thick side wall segment 20a intermediate of the opposite ends and an annular shoulder or recess 21 is formed on the outer surface of the thick wall segment to receive the open inner end of the inner end cap 22 when assembled therewith. After a sterilized needle 16 and mount 18 is initially packaged in a protective enclosure (comprising an outer end cap 20 and an assembled inner end cap 22, which caps have also been sterilized), an exterior seal 24 is attached to extend across the joint at the shoulder 21 between the assembled needle caps. Damage or removal of the seal is indicative of tampering or an unsafe or unsterilized condition. When a user sees that the seal is broken, the disposable needle assembly 10 should not be used and should be thrown away and disposed of in a proper manner.

At the inner, open, end the outer end cap 20 is provided with a relatively thin annular wall segment 20b which forms a socket for slidably receiving a plurality of radially outwardly extending vanes or ribs 18a of the needle mount 18. The vanes 18a are equilaterally spaced around a central hub portion 18b and dimensioned to fit longitudinally inside the bore of the thin-walled open inner end section 20b of the outer end cap 20 when the cap is assembled onto the outer end portion of the needle as shown in FIGS. 1 and 2.

As illustrated in FIGS. 2a and 2b, the radial vanes 18a are integrally joined with the central cylindrical hub 18b which is molded in place around the exterior of the elongated hollow metal needle 16. The needle mount 18 also includes a thin, radial disc portion 18c of generally circular shape and integrally joined with the vanes 18a and the cylindrical hub 18b as shown in FIG. 5. The disc portion has an outer diameter slightly greater than the distance between opposite edges of opposed sets of vanes 18a and an outer edge portion serves as an end stop for engaging the open end of the thin-walled section 20b of the outer end cap when the outer end portion of the needle 16 is inserted into the cap. The disc 18c of the needle mount also includes a plurality of radially outwardly extending, equilaterally disposed drive arm elements 18d spaced around the circumference of the disc. On an opposite side of the disc 18c the needle mount 18 is provided with a short, externally threaded section 18e and an elongated rubber envelope 26 enclosing the inner end portion 16b of the needle is secured to a body portion 18f of the needle mount adjacent the threaded section by an annular clinching band 28.

The rubber envelope 26 is closed at the outer end adjacent the sharp inner end 16c of the hollow needle 16 and when the fluid collecting or dispensing tube 14 is forced inwardly into the tube holder 12 as indicated by the arrow A in FIG. 3, the sharp tip 16c pierces the rubber envelope and the body of the rubber envelope is compressed in annular rings between the tube holder 12 and tube 14 around the inner end portion 16b of the needle during fluid collection or dispensing operations. Subsequently, when the tube 14 is withdrawn from the tube holder 12 in a direction opposite the arrow A, the rubber envelope 26 rebounds to extend outwardly around the needle to again shield and enclose the inner end portion of the needle and thus prevent the inadvertent dispersant or escape of fluids from the needle into the surrounding environment.

In accordance with the present invention, the elongated tube holder 12 is provided with an annular forward end wall 30 having a centrally positioned threaded aperture 30a formed in a thickened wall portion 30b and adapted to receive the threaded portion 18e of the needle mount 18 when the inner end portion 16b of a needle is inserted into the interior of the tube holder. The tube holder also includes an elongated tubular body portion 32 having a pair of radial ears 32a at the opposite, open end to facilitate handling of a tube holder for dispensing or receiving fluids with a tube 14 inserted therein and a needle 16 mounted in place.

In accordance with a feature of the present invention, a hollow sleeve 34 formed of molded plastic material is mounted for rotation on the body of the tube holder 12 adjacent a forward end portion. The sleeve 34 includes a large diameter annular skirt wall portion 36 extending lognitudinally on the tube holder body from the forward end wall 30 toward the ears 32a and the skirt wall has a knurled outer surface 36a to facilitate manual rotation of the skirt wall on the body in either direction as indicated by the arrow B in FIG. 2 and the arrow C in FIG. 3.

At the forward end, the skirt wall 36 is integrally joined to a radially inwardly directed annual wall 38 spaced outwardly of the annular end wall 30 of the tube holder 12. The annular end wall 38 in turn is integrally joined to an outwardly extending socket-wrench-like annular wall 40 which is open at the outer end to receive the needle 16 and mount 18 and the open-ended thin-wall segment 20b of the outer end cap 20. The socket-wrench wall 40 is mounted for rotation on the thick central wall portion 30b of the forward end wall 30 of the tube holder and these members are free to rotate relative to one another in either direction but are restrained against relative longitudinal movement by an annular retaining ring 42 which seats in facing annular grooves provided in the outer side surface of the thick wall 30b and the inner surface of the socket wall 40, respectively.

The open-ended socket wall 40 is formed with a plurality of elongated, longitudinally extending drive slots 40a which are open at the outer end of the wall and spaced equilaterally around the circumference of the wall to receive the radial drive arms 18d of a disk 18c of a needle mount 18. As illustrated in FIG. 3, the inside diameter of the socket wall 40 is slightly larger than the outside diameter of the open-end portion 20b of the outer end cap 20 and also is larger than the outer diameter of the circular portion of the disk 18c of a needle mount 18 carried thereby during insertion of a needle into the tube. This arrangement permits the outer end cap 20 to be used for turning the threaded segment 18e of the mount 18 into the threaded aperture 30a of the forward end wall 30 of the tube holder 12. Accordingly, the outer end cap 20 is not removed from the needle 16 and mount 18, until the mount is fully threaded into place and only just prior to actual use of the needle. Alternatively, the sleeve 34 can be manually rotated as indicated by the arrow B in FIG. 2 to thread the needle mount into place once the drive arms 18d of the disk 18c are engaged in the open ends of the socket wall slots 40a.

Of course, before a needle 16 and mount 18 are secured to the tube holder 12 as described, the inner end cap 22 is manually withdrawn as indicated by the arrow D in FIG. 1 and the uncovered inner end portion of the needle assembly is inserted into the open-ended socket wall 40 and the aperture 30a as indicated by the arrow E while the body of the protective tube holder 12 is firmly grasped.

In accordance with a feature of the invention, either the sleeve 34 may be manually rotated (arrow B) as shown in FIG. 2 to thread the needle mount 18 into the tube holder or the needle mount may be driven to rotate (arrow F) by rotating the outer end cap 20 which is still in place on the needle mount and protectively enclosing the outer end portion of the needle 16.

In the latter case, a one-way slip clutch drive connection is utilized between the assembled outer end cap 20 and the needle mount 18 and this is illustrated best in FIGS. 2a and 2b. Referring to FIGS. 2 and 2a, the thin-walled open end portion 20b of the outer end cap 20 is formed with a pair of diametrically opposed, longitudinally extended and radially inwardly directed ribs 23 which are adapted to engage the vanes 18a of the needle mount 18 to drive the mount in a clockwise direction (arrow G) when the outer end cap is rotated in a clockwise direction as indicated by the arrow F (FIG. 2) and the arrow H (FIG. 2a). In this mode, driving contact is established along radially extending contact surfaces on the ribs 23 of the outer end cap 20 and one pair of ribs or vanes 18a on the needle mount 18 adjacent the outer edges thereof.

Removal or unthreading of a mounted needle from the tube holder after use may not be accomplished by re-replacement of the outer end cap 20 on the needle 16 followed by rotating the cap in a counterclockwise direction because of the one-way clutch system best illustrated in FIGS. 2 and 2b. The ribs 23 are formed on the open-ended wall section 20b of the outer end cap 20 adjacent a pair of diametrically opposite, L-shaped slots 25 formed in the wall section with longitudinal slot legs 25a running parallel and closely adjacent the ribs and open at the end of the thinwall section. The slots 25 also include short, radially extending slot legs 25b intersecting and transverse to the longitudinal slot legs 25a. Each L-shaped slot thus forms a radially outwardly deflectable base wall segment or finger 44 on which an outer end portion of a rib 23 is provided. If the outer end cap 20 is rotated in the direction as shown by the arrow I in FIG. 2b in an attempt to unthread the needle mount 18, the fingers 44 are deflected radially outwardly by contact between the ribs 23 and the outer edges of the vanes 18a of the needle mount 18. Thus, only the sleeve 34 can be utilized to unthread a mounted needle after use, and this can be accomplished with one hand by rotating the sleeve in a counterclockwise direction as indicated by the arrow C in FIG. 5. This feature discourages users from attempting to remount the outer end cap 20 on a used or contaminated needle for the purpose of detaching the used needle from the tube holder 12.

When the needle mount 18 is unthreaded by rotation of the sleeve, the drive arms 18d move outwardly in a longitudinal direction toward the open ends of the open-ended slots 40a until the threaded segment 18e of the needle mount 18 is completely disengaged from the threaded aperture 30a in the forward end wall 30 of the tube holder 12. At this time, the disposable used needle 16 and mount 18 is free to drop away (arrows J) from the reusable tube holder 12 into an awaiting receptacle.

The disposable needle apparatus in accordance with the invention provides a safe, sterile and easy-to-use system which substantially eliminates the possibility of needle stick injuries. Direct manual contact between a contaminated/used needle is eliminated and inadvertent injuries prior to needle usage are substantially eliminated.

The sterilized needle 16 and mount 18 are packaged in a sterile enclosure comprising an outer end cap 20 and an inner end cap 22 which are assembled together and provided with a seal 24. As a first step in preparation for use, the inner end cap is withdrawn (arrow D - FIG. 1) and the seal 24 is broken. The needle 16, mount 18 and outer end cap 20 are aligned with the tube holder 12 and the uncapped inner end portion 16b of the needle with the rubber enclosure 26 thereon is inserted into the awaiting threaded aperture 30a through the annular socket wall 40 of the sleeve 34 (arrows E -FIG. 2). When the uncovered threaded segment 18e of the needle reaches the threaded aperture, the needle cap 20 is rotated in a clockwise direction (arrow F) or the sleeve 34 is similarly rotated (arrow B) until the threaded engagement is complete. A tube 14 is then inserted into the open end of the tube holder 12 (arrow A - FIG. 3) and the inner end 26c of the needle pierces the forward end wall of the tube as the rubber cover 26 is compressed between the wall 30 and the forward end of the tube. The assembled needle 16, tube holder 12 and tube 14 is now ready for use.

Just prior to use, the outer end cap 20 is withdrawn (arrow K - FIG. 3) from the outer end portion of the fully mounted needle 16 to expose the needle tip 16a for the first time. After use, the contaminated/used needle is released from the tube holder 12 without requiring any manual contact with or near the needle 16 or the needle mount 18 by rotating the sleeve 34 in a counterclockwise direction (arrow C - FIG. 5) relative to the tube holder body 32. This can be done with one hand while holding the tube holder pointed downwardly over an awaiting receptacle. While the needle is pointed downwardly, after the threaded segment 18e of the needle mount 18 becomes disengaged from the threaded aperture 30a of the tube holder 12, the needle 16 and mount 18 become free of the tube holder and simply drop downwardly into the receptacle. The tube 14 may be withdrawn rearwardly from the openend of the tube holder 12 before or after the needle mount 18 is unthreaded from the tube holder. The used tube holder 12 may be sterilized and reused or can be disposed of after use, if desired.

At no time during the preparation, use or disposal of the needle system is the user's hand required to be in close proximity to an uncovered end portion or sharp point 16a or 16b of the needle 16 or the needle mount 18 and accordingly, inadvertent needle stick injuries are substantially eliminated with the disposable needle system 10 of the present invention.

Although the present invention has been described in terms of a preferred embodiment, it is intended to include those equivalent structures, some of which may be apparent upon reading this description, and others that may be obvious after study and review.

What is claimed and sought to be secured by Letters Patent of the United States is:

1. Disposable needle apparatus for receiving/dispensing fluids such as body fluids, medicaments, vaccines and the like, comprising:
    hollow needle means having an open outer end for receiving/dispensing said fluids and an inner end portion open at an inner end;
    threaded mounting means on said needle means intermediate said ends thereof;
    housing means having a threaded portion on a forward wall thereof for threadedly engaging and supporting said mounting means when said inner end portion of said needle means is inserted in said housing; and
    annular socket wrench means permanently mounted on said housing means for rotation about said threaded portion adjacent said forward wall of said housing means and detachably engageable with said mounting means for unthreading said needle means relative to said housing means to disengage said needle means from said housing means after use.

2. The disposable needle apparatus of claim 1 wherein said annular socket wrench means includes an open forward end for receiving said mounting means of said needle means for turning said mounting means on said threaded portion on said forward wall.

3. The apparatus of claim 1, wherein:
    said mounting means includes at least one radial arm and said socket wrench means includes at least one slot extending longitudinally of said housing means and open at said forward end to receive said radial arm and turn said mounting means upon rotation of said socket wrench means on said housing means.

4. The disposable needle apparatus of claim 3, wherein said socket wrench means is secured to rotate on said housing means and is retained against axial movement thereon relative to said aperture for turning said mounting means in said threaded portion of said forward wall.

5. The disposable needle apparatus of claim 4, wherein:
    said mounting means includes a plurality of said radial arms spaced equilaterally around said needle means and said socket wrench means includes a plurality of said slots for receiving said arms to rotate said mounting means relative to said housing means by turning said socket wrench means on said housing means.

6. The disposable needle apparatus of claim 1, including;
    removable outer end cap means for enclosing a portion of said needle means extending from said mounting means to said outer end, and
    one-way clutch means operatively engageable between said outer end cap means and said mounting means for transmitting rotating movement in one direction from said outer end cap means to said mounting means for threading said needle mounting means into said threaded portion of said housing means.

7. The disposable needle apparatus of claim 6, wherein;
    said one-way clutch means provides slippage between said outer end cap means and said mounting means whereby rotation of said outer end cap means in an opposite direction does not unthread said mounting means from said threaded portion of said housing means.

8. The disposable needle apparatus of claim 7, wherein;
said one-way clutch means includes a drive element on said outer end cap means engageable to drive a driven element on said mounting means when said outer end cap is rotated in said one direction.

9. The disposable needle apparatus of claim 8, wherein;
said drive element is movable out of driving engagement with said driven element when said outer end cap means is rotated in said opposite direction.

10. The disposable needle apparatus of claim 9, wherein;
said drive element and said driven element include engageable drive surfaces extending radially outwardly of said hollow needle means; and
wherein said drive element is flexible to move said drive surface thereof away from driving engagement with said drive surface of said driven element upon rotation of said drive element in said opposite direction.

11. The disposable needle apparatus of claim 8, wherein;
said driven element comprises at least one radial rib integrally formed on said mounting means and projecting outwardly of said needle means, and
said drive element comprises a hollow annular wall for receiving said mounting means and slidably engaging an outer edge of said rib for holding said outer end cap means in place in an enclosing position around said outer end portion of said needle means, said drive element having at least one radially inwardly projecting rib for driving engagement with said rib of said driven element upon rotation of said outer end cap means in said one direction.

12. The disposable needle apparatus of claim 11, wherein;
said rib of said outer end cap means and said rib said mounting means are moved into driving engagement during rotation of said end outer end and cap means in said one direction, and
at least one of said ribs is movable radially of said needle means out of driving engagement with the other of said ribs upon rotation of said outer end cap means in said opposite direction.

13. The disposable needle apparatus of claim 11, wherein;
said annular wall includes at least one wall segment that is flexible in a radial direction adjacent said rib thereon for permitting said rib to move radially out of driving engagement with said rib of said mounting means when said outer end cap means is rotated in said opposite direction.

14. The disposable needle apparatus of claim 13, wherein;
said flexible wall segment is formed by an L-shaped slot in said annular wall having one leg extending along said radial rib thereof and a second leg intersecting said one leg and extended transverse thereto.

15. The disposable needle apparatus of claim 6, wherein;
said removable outer end cap means includes an elongated hollow body having a closed outer end adjacent said outer end of said needle means and an open opposite inner end for slidably receiving said mounting means of said needle means inserted therein.

16. The disposable needle apparatus of claim 15, wherein;
said annular socket wrench means on said housing means includes an open forward end for receiving said opposite inner end of said outer end cap means with said mounting means engaged therein whereby said mounting means may be threaded into said threaded aperture of said housing means upon rotation of said mounting means in said one direction.

17. The disposable needle apparatus of claim 16, wherein;
said mounting means is threaded into said threaded portion of said housing means by rotational torque in said one direction applied to said outer end cap means, and
wherein said outer end cap means is removable from engagement with said mounting means and from said socket wrench means by sliding movement longitudinally outwardly thereof.

18. The disposable needle apparatus of claim 16, including;
rotative drive means engageable between said socket wrench means and said mounting means when said needle means is inserted longitudinally into said socket wrench means whereby said mounting means is threaded onto said threaded portion of said housing means by rotation of said socket wrench means thereon in said one direction.

19. The disposable needle apparatus of claim 18, wherein;
said drive means comprises a radial drive arm on said mounting means outside of said outer end cap means and slidably disposed in an open ended slot of said socket wrench means for rotating said mounting means upon rotation of said socket wrench means while pemitting relative movement therebetween longitudinally of said needle means.

20. The disposable needle apparatus of claim 15, including;
a removable inner end cap for enclosing said inner end portion of said needle means, said inner end cap having an elongated hollow body with a closed outer end adjacent said inner end of said needle means and an open inner end slidably engageable with said opposite inner end of said outer end cap means to provide a protective enclosure for said needle means and mounting means when said end caps are assembled together.

* * * * *